United States Patent [19]

Lekawa

[11] Patent Number: 4,486,177
[45] Date of Patent: Dec. 4, 1984

[54] CROWN REMOVAL TOOL

[76] Inventor: Raymond E. Lekawa, 302 S. Alandale Ave., Tucson, Ariz. 85710

[21] Appl. No.: 423,019

[22] Filed: Sep. 24, 1982

[51] Int. Cl.$^3$ .............................................. A61C 3/00
[52] U.S. Cl. ..................................... 433/161; 433/218; 29/239
[58] Field of Search ................. 433/154, 155, 156, 39, 433/152, 153, 161, 162, 218; 29/239, 256, 258, 259, 263, 264; 254/234

[56] References Cited

U.S. PATENT DOCUMENTS

| | | | |
|---|---|---|---|
| 425,650 | 4/1890 | Bing | 433/145 |
| 606,460 | 6/1898 | Ivory | 433/39 |
| 1,349,464 | 8/1920 | Lancit et al. | 433/145 |
| 1,357,870 | 11/1920 | Hume | 81/9.3 |
| 2,220,103 | 11/1940 | Hanssen | 433/154 |
| 3,426,752 | 2/1969 | Laico | 29/239 |
| 4,179,816 | 12/1979 | Anderson | 433/161 |
| 4,196,520 | 4/1980 | Hoffman | 433/218 |

FOREIGN PATENT DOCUMENTS 400139  10/1933  United Kingdom .................. 81/9.3

Primary Examiner—John J. Wilson

[57] ABSTRACT

A crown removal tool comprising an elongated hollow cylindrical body having at one end perpendicularly protruding tangs and a slot opening formed therebetween, the tangs adapted to engage one side of a groove formed in a patient's tooth crown, the device additionally comprising an inner rod slidable in the central elongated opening of the hollow cylindrical body, the inner rod having at one end a perpendicularly protruding tang slidably residing in the slot formed between the pair of tangs attached to the hollow cylindrical body, the inner rod tang adapted to engage the other side of the groove formed in a patient's tooth crown, the other end of the inner rod being threaded and having a rotatable nut thereon, the nut adapted to be screwed against the end of the hollow cylindrical body whereby rotation of the nut while engaging the end of the hollow cylindrical body draws the tang attached to the inner rod away from the tangs attached to the hollow cylindrical body. A cap unit resides on the end of the inner body threaded end to limit movement of the threaded nut so that when the threaded nut is against the cap end, the tang of the inner rod aligns with the tangs of the cylindrical hollow body and the tool tangs may be placed in the crown groove whereupon by screwing of the rotatable nut, the tangs are forced apart and the crown fractured which permits its removal.

5 Claims, 10 Drawing Figures

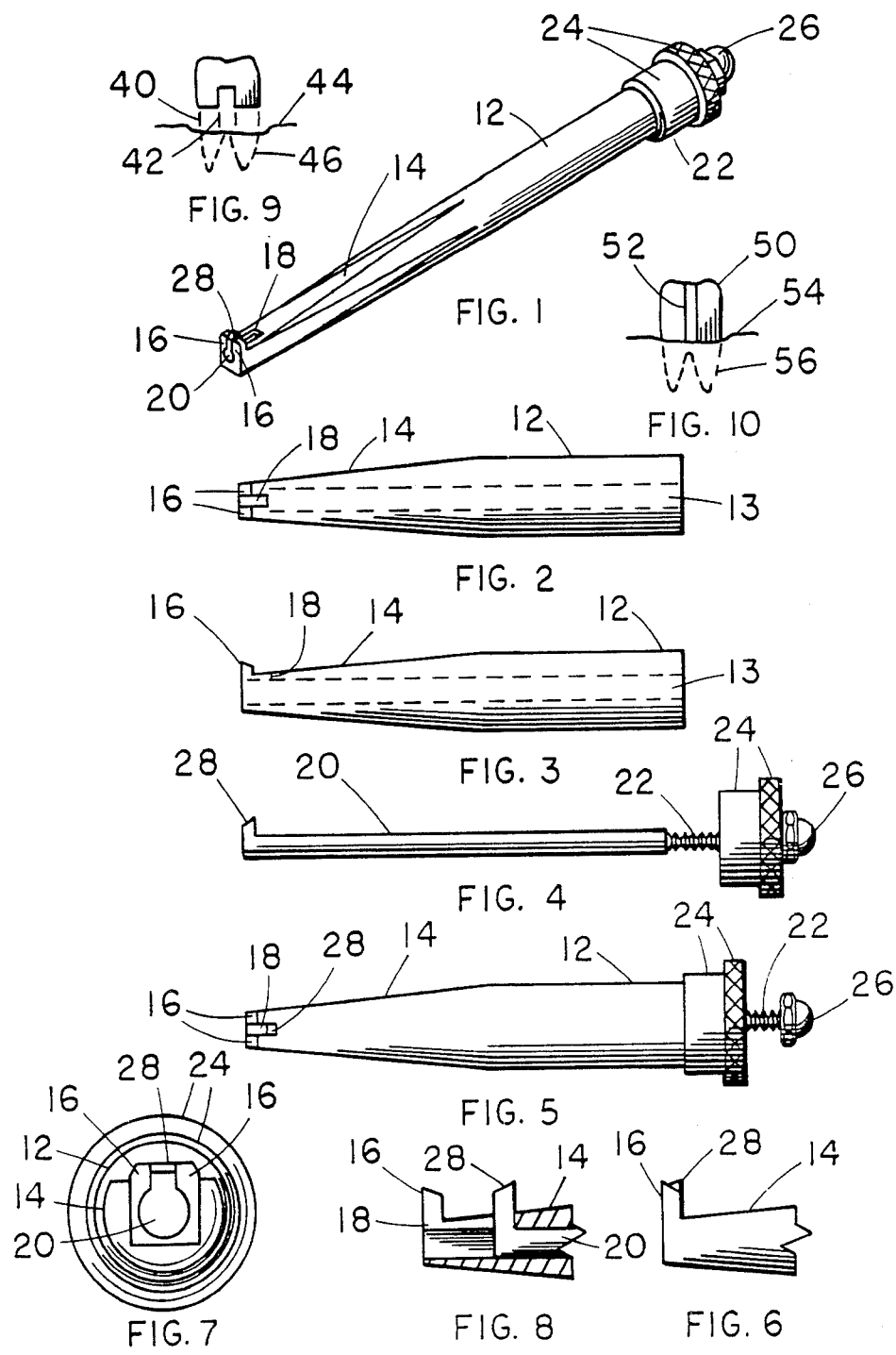

CROWN REMOVAL TOOL

BACKGROUND OF THE INVENTION

This invention relates to a tool by which crowns in patient's mouths may be fractured and easily removed.

With the advance of denistry, it has become possible to replace a person's tooth with a crown which may be made of a metal, such as gold, or may be constructed of plastic or a ceramic, the crown being shaped like the tooth it replaces. In doing so, the common practice is for a dentist to leave the roots of the tooth which is to receive the crown in place, and to grind or otherwise remove the tooth above the gum line, leaving only a centrally located stub to be capped by the crown. In most cases, to enhance appearances, the portion of the tooth removed would extend slightly below the gum line so that the crown which is placed on the tooth would rise from a point slightly below the gum level in order that no line be showing between the tooth from the crown.

Prior to the crown being emplaced upon the remaining stub of the tooth, a cavity interiorly to the crown is filled with fast drying epoxy and then the filled cavity is inverted over the tooth stub and the crown aligned. The epoxy, being fast drying, adheres to the stub of the tooth, as well as to the interior portion of the crown, and the emplacement is complete. Of course before all work is commenced, all areas are made antiseptic.

It becomes necessary, from time to time, to remove prior placed crowns from patient's teeth because of infection, decay, or the like, of the tooth. The present method of crown removal is to split the crown in two by making three cuts or slots (actually accomplished by grinding) in the crown, vertical cuts or slots on opposite sides of the crown plus one across the top of the crown to join the other two. This tends to form a line to fracture which goes completely up and over and down the tooth. Next, the dentist will try to separate the crown into two halves along the slot formed by fracturing, either by breaking with a chisel and hammer, or perhaps by placing a screwdriver or similar tool into the slot and then twisting the screwdriver sideways.

Regardless of which method is utilized by the dentist, the pain to the patient is obviously excruciating.

It also becomes necessary from time to time for a patient's tooth to be removed where the root structure has become deformed. In the present dental practice the tooth is commonly split into two or more pieces when the tooth has more than one root in order that a portion of the tooth most directly connected to each root may be extracted separately.

Currently the practice is to fracture the tooth using a hammer and chisel directly upon the top of the tooth, or, in many cases, cutting slots in the tooth vertically on opposite sides and across the top connecting the opposite side slots at which time the dentist will then fracture with a hammer and chisel in the slot, or by turning a screwdriver sideways in the slot. The tooth then fractures along the slot lines. Again, as in crown removal, this is obviously excruciatingly painful to the patient.

It is to the easy fracturing and removal of crowns to which the subject invention is directed.

SUMMARY OF THE INVENTION

In accordance with the present invention, means are provided for fracturing a crown of a tooth in order that the crown may be easily removed when necessary.

The crown removal tool which is disclosed comprises an elongated hollow cylindrical body having at one end two perpendicularly protruding tangs, the tangs separated by a slot opening which communicates between the central hole of the cylindrical body and the outside. Residing slidably interiorly to the cylindrical body hole is an inner rod, one end of which also has a perpendicularly protruding tang adapted to slidably reside in the slot between the cylindrical body pair of tangs. The other end of the inner rod is threaded with a rotatable nut thereon, the rotatable nut adapted to engage the end of the cylindrical body.

The two perpendicularly protruding tangs of the cylindrical body and the one perpendicular protruding tang of the inner rod are aligned and then inserted into a slot cut vertically in one side of the crown, the tangs engaging opposite sides of the slot.

After the tangs have engaged opposite sides of the slot, the tangs are made to separate by rotating the rotatable nut upon the thread of the inner rod, the inner rod then advancing in a direction towards the rotating nut and pulling the tang attached thereto in the slot of the cylindrical body.

As the tangs pull apart, while engaging the sides of the slot of the crown, the crown is caused to fracture, breaking the epoxy interiorly to the crown attached to the underlying tooth stub and separating the crown and the epoxy from the tooth stub.

Similarily, the device may be used to fracture a tooth to facilitate removal of the tooth, including its roots. To accomplish such, a vertical slot may be cut in the tooth, and then the tangs of the subject device placed into the slot, the rotatable nut turned, and the tooth then pulled apart, or fractured, along a line including the slot.

To facilitate the engagement of the sides of the crown, or the tooth, by the tangs of the subject device, the tangs each have one slanted side so as to form a sharpened edge or cutting teeth at the end of the tangs.

Accordingly, it is an object of the subject device to provide a means by which a great amount of force may be applied to a crown such as to fracture that crown and break it away from the stub of the tooth.

It is also an object of the subject invention to provide a means by which in a small area large forces may be exerted side to side on a groove formed in the crown may be used to fracture the crown.

Other objects of the invention will in part be obvious and will in part appear hereinafter. The invention accordingly comprises the apparatus possessing the construction, combination of elements, and arrangements of parts which are exemplified in the following detailed disclosure, and the scope of the Application which will be indicated in the claims.

BRIEF DESCRIPTION OF THE DRAWINGS

For further understanding of the nature and objects of the present invention, reference should be had to the following detailed description taken in connection with accompanying drawings wherein:

FIG. 1 is a perspective view of the subject crown removal tool;

FIG. 2 is a top view of the hollow cylindrical body of the subject device;

FIG. 3 is a side view of the subject hollow cylindrical body of the subject device;

FIG. 4 is a side view of the inner rod portion of the subject device;

FIG. 5 is a top view of the subject crown removal tool;

FIG. 6 is a partial side view of the crown engaging portion of the subject device;

FIG. 7 is an end view of the crown engaging portion of the subject device;

FIG. 8 is a partial side view of the crown engaging tangs in full extention;

FIG. 9 is a perspective view of a crown upon a patient's tooth; and

FIG. 10 is a perspective view of a patient's tooth in a patient's mouth.

In the various views, like index numbers refer to like elements.

DETAILED DESCRIPTION OF THE PREFERRED EMBODIMENT

Referring now to FIG. 1, a perspective view of the subject tooth crown removal tool 10 is shown. Primarily, the subject device comprises an elongated hollow cylindrical body 12 having a tapered portion 14 with tangs at the end protruding transversely thereto, and at the other end of hollow cylindrical body 12, an inner rod 20 emerging from the cylindrical body 12 central opening, the rod having knurled nut 24 screwed on threads 22 thereon, and a cap nut 26 (not shown) terminating the threaded end of inner rod 20. The tangs shown comprise two body tangs 16 on opposite sides of the inner rod tang 28 attached perpendicularly to inner rod 20, inner rod tang 28 adapted to slidably reside in slot opening 18 of cylindrical body 12.

Referring briefly to FIG. 2, a top view of body 12 is shown comprising the cylindrical body 12, the tapered portion 14 narrowing down to its smallest end where are located body tangs 16 on opposite sides of centrally located slow opening 18. It is through slot opening 18 that the inner rod tang 28 (FIG. 4) slides. Shown in dotted fashion in FIG. 2 is the hole 13 that runs longitudinally through the hollow body elongated cylinder, hole 13 adapted to slidably receive the inner rod 20.

Now referring briefly to FIG. 3, a side view of the cylindrical body 12 of the subject tool is shown detailing from right to left central hole 13 (in dotted form) running through the total length of body 12. Tapered portion 14 narrows from a point near the center of body 12 to the opposite end where, rising perpendicularly to the longitudinal axis of body 12 is one of the body tangs 16. Body tang 16 comprises teeth-like upward protrusion having a slight slant backwards (exaggerrated in FIG. 3) to form a sharpened edge which is helpful in engaging the slot formed in the tooth crown as will be discussed later. There are two body tangs in body 12, the view of FIG. 3 showing one of the body tangs with the other body tang hidden behind it.

Referring now to FIG. 4, a side view of inner rod 20 is detailed showing from right to left, cap nut 26 terminating the end of the threaded portion 22 of inner rod 20, followed by knurled nut 24 and the visible threads 22. The main body of inner rod 20 continues to the left where it ends, then terminating in a perpendicularly protruding tooth, or tang referred to as the inner rod tang 28. Inner rod tang 28 is adapted to ride in slot opening 18 of body 12. Inner rod tang 28 rises straight a short distance, nominally the distance of the diameters of the inner and outer circumference of the end of tapered portion 14 where, at which time the tang 28 slants (exaggerrated in FIG. 4) towards the opposite end of inner rod 20 to form a sharpened edge. The purpose for this, as will be made more clear in explanation of how the tool operates, is to better engage the side of the slot formed in the crown to be removed. The diameter of inner rod 20 is closely matched to the diameter of hole 13 in order that there be minimum amount of looseness. The maximum diameter of thread 22 is smaller than the diameter hole 13 in order that the threads will not impede movement of inner rod 20 in hole 13.

Referring now to FIG. 5, a top view of the completely assembled crown removal tool 10 is illustrated comprising from right to left cap nut 26, knurled nut 24, threads 22, all on inner rod 20, followed by the body 12 of the hollow cylinder and its tapered portion 14. At the far end is body tangs 16 on opposite sides of slot opening 18. At the end of slot opening 18 distal from body tangs 16 is upward protruding inner rod tang 28.

It is important to notice that the distance which inner rod tang 28 has moved to the right from its position adjacent to body tangs 16 is approximately equal to the distance between the end of knurled nut 24 and the cap nut 26. This is an adjustment which is made when the tool is assembled by placing the cap nut 26 on the threads 22 of inner rod 20 at the appropriate place, and then securing cap nut 26 in place with an epoxy. The purpose for this is so that knurled nut 24 may be screwed against cap nut 26, and then knurled nut (along with cap nut 26 and inner rod 20) pushed to the left and all the tangs align themselves in a straight line. The tool then is ready to use when placing all three tangs in the slot cut in the crown that is to be removed.

Referring now to FIG. 6, a partial side view of the end of tapered portion 14 is detailed where the knurled nut 24 is next to cap nut 26 and has been pushed against the end of body 12 such that inner rod tang 28 is in alignment with body tangs 16. As can be seen, the outward slanted side of body tangs 16 is shown in exaggerrated view, as well as the inward slanted side of inner rod tang 28. The dotted line which continues upward from the end of the body 12 is the outside portion of inner rod tang 28.

Referring now to FIG. 7, an end view of the tapered end of 14 is shown where, starting from the center, is seen the end of inner rod 20 with inner rod tang 28 protruding upward through the slot formed between body tangs 16. Moving outward, the next almost completed circle is the end of tapered portion 14 showing the body tangs 16 riding perpendicularly from the circumference of tapered portion 14. Following the end of tapered portion 14 is the circle showing the circumference of body 12. Body 12 terminates then with the next two circles showing the edge and part of the face of knurled nut 24, knurled nut 24 also shown by the largest outside circle representing the peripheral edge of the knurling on the outside of knurled nut 24.

Referring briefly now to FIG. 8, an end view of tapered portion 14 is shown in an exaggerrated and expanded side view where the inner rod tang 28 is at its maximum separation from body tangs 16. At this point, and if the inner rod tang 28 and the body tangs 16 had been set to engage the sides of the slot formed in a crown, the tangs would be at their fartherest point apart and in doing so, be pulling the slot apart in the crown, and spreading the crown. Shown in dotted fashion is the inner hole 13, and the inner rod 20. The end of inner rod 20 is shown rising up to the outside most portion of inner rod tang 28, with the opposite planted side of inner rod tang 28 connecting with inner rod 20.

Finally, referring now to FIG. 9, a perspective view of a crown upon a tooth is detailed. Beginning at the lower-most part, the remaining tooth 46 is shown with its roots, rising to a small stub portion which has been rounded by the dentist, the stub portion rising above the gum line 44. Crown 40, which has a cavity interiorly, is shown immediately over the top of tooth 46. When a crown is placed over the ground down portion of tooth 46, the interior cavity, which had been filled with an epoxy, causes the crown to adhere to the top of the tooth. Shown in crown 40 is a slot 42 which has been cut or ground vertically in the tooth. When this slot is cut, its width is sufficient that the crown removal tool 10 body tangs 16 and inner rod tangs 28 will fit into it, as the tool is aligned in a direction substantially perpendicular to the direction of the slot. For a patient sitting in a dental chair with tooth 46 substantially vertical, the subject crown removal tool 10 will be substantially horizontal. The sharpened edges at opposite sides of the top-most portion of both body tangs 16 and inner rod tangs 28 must reside below the outside surface of the tooth. At this point, it is obvious to see the purpose for slanting the inside and outside faces of both tangs in order that the tool might best engage the sides of the slot 42 and resist slipping out. Additionally, the depth of slot 42 cut into crown 40 must be sufficient so enough of body tangs 16 and inner rod tangs 28 may grasp the sides of the slot of crown 40 so that possibility of chipping of the sides of slot 42 is lessened.

With the crown removal tool in place, with inner rod tang 28 aligned with body tangs 16, the face of knurled nut 24 will be against the end of body 12 and cap nut 26 against knurled nut 24. Then the dentist, holding body 12 by the fingers of one hand, proceeds to rotate knurled nut 24 against the end of body 12. Since inner rod 20 is held from rotating by virtue of inner rod tangs 28 sliding in slot opening 18 of tapered portion 14, as knurled nut 24 is rotated inner rod tangs 28 will move along in slot 18 towards the opposite end of the crown removal tool. The separation of the body tangs 16 and inner rod tang 28, while engaging the sides of slot 42, will spread the slot in the crown, causing the crown to fracture along the slot, across the top away from slot 42, and along the opposite vertical side. Once the crown has fractured across the top and opposite side, as well as at the slot 42, and since the epoxy interiorly the cavity of the crown stays with the crown, it also will fracture substantially along the same lines as the crown, and thus separate from the rounded off portion of tooth 46. Once the epoxy has separated from tooth 46, the crown is merely lifted off (if it stays in one piece), or it will have already fallen off into two pieces.

It is noted that the same identical technique may be used to split a tooth as shown in FIG. 10.

For example, referring briefly to FIG. 10, a tooth 50 is shown in place with roots 56 below gum line 54. Cut vertically in tooth 50 is a slot 52 adapted to receive crown removal tool 10. Here the same technique is utilized as above, the inner rod tang 28 and body tangs 16 inserted into the groove, and then forced apart. Such would cause the tooth to split facilitating removal by the dentist of each tooth portion plus its accompanying root.

Since the tool in this preferred embodiment is completely constructed of stainless steel, it is easily sanitized in an autoclave, or antiseptic solution for repeated use upon different patients.

While a preferred embodiment of Applicant's apparatus has been shown and described, it is appreciated that still other embodiments of the invention are possible and that there is no intent to limit the invention by such disclosure, but rather it is intended to cover all modifications and alternate embodiments falling with the spitit and the scope of the invention as defined by the appended claims.

I claim:

1. A crown removal tool for removing crowns from patient's teeth comprising:
    an elongated hollow cylindrical body having a first and second end;
    a pair of transversely protruding spaced apart tangs attached at the first end of said elongated cylindrical body;
    an elongated slot formed between said spaced apart tangs;
    an inner rod slidable in said elongated cylindrical body, said inner rod having a first and second end; and
    a transversely protruding tang attached to the first end of said inner rod, said tang adapted to slidably reside in said elongated slot, said pair of spaced apart tangs of said elongated hollow cylindrical body and said tang of said inner rod adapted to engage opposite sides of a groove formed in the patient's tooth crown where by sliding said inner rod in said hollow cylindrical body, said tangs are separated and thus separate the sides of the groove in the crown causing the crown to fracture and separate from the patient's tooth.

2. The crown removal tool as defined in claim 1 wherein said inner rod additionally comprises:
    a threaded second end; and
    a rotatable nut thereon, said nut adapted to be screwed upon said inner rod threads against the end of said elongated hollow cylindrical body whereby in doing so, said inner rod moves longitudinally through said elongated cylindrical body and thereby causes the tang attached thereto to move relative to the tangs of the elongated hollow cylindrical body.

3. The crown removal tool as defined in claim 2 wherein said slidable inner rod additionally comprises:
    a cap nut residing on said inner rod threaded end next to said rotatable nut whereby one direction of the longitudinal travel of said rotatable nut is limited by said cap nut.

4. The crown removal tool as defined in claim 3 wherein said elongated cylindrical hollow body transversely protruding tangs include a sharpened edge at the end of said tangs, said sharpened edge adapted to better engage the side of the groove formed in the patient's tooth crown.

5. The crown removal tool as defined in claim 4 wherein said inner rod transversely protruding tang further comprises:
    a sharpened edge at the end of said tang adapted to better engage the side of the groove formed in the person's crown.

* * * * *